(12) United States Patent
Matsuzawa

(10) Patent No.: US 9,668,330 B2
(45) Date of Patent: May 30, 2017

(54) GANTRY OF X-RAY CT SYSTEM

(71) Applicant: TOSHIBA MEDICAL SYSTEMS CORPORATION, Otawara-shi (JP)

(72) Inventor: Yohei Matsuzawa, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 104 days.

(21) Appl. No.: 14/144,842

(22) Filed: Dec. 31, 2013

(65) Prior Publication Data

US 2014/0119503 A1 May 1, 2014

Related U.S. Application Data

(63) Continuation of application No. PCT/JP2012/071439, filed on Aug. 24, 2012.

(30) Foreign Application Priority Data

Aug. 26, 2011 (JP) .................... 2011-184828

(51) Int. Cl.
| | | |
|---|---|---|
| *H05G 1/02* | (2006.01) | |
| *A61B 6/03* | (2006.01) | |
| *G01N 23/04* | (2006.01) | |
| *A61B 6/00* | (2006.01) | |
| *F16C 35/067* | (2006.01) | |

(52) U.S. Cl.
CPC .............. *H05G 1/02* (2013.01); *A61B 6/035* (2013.01); *G01N 23/046* (2013.01); *A61B 6/4488* (2013.01); *F16C 35/067* (2013.01); *F16C 2226/60* (2013.01); *F16C 2300/14* (2013.01)

(58) Field of Classification Search
CPC ......... A61B 6/06; A61B 6/035; A61B 6/4488; F16C 35/067; F16C 2226/60; F16C 2300/14; G01N 23/046; H05G 1/02
See application file for complete search history.

(56) References Cited

U.S. PATENT DOCUMENTS

| | | |
|---|---|---|
| 5,982,844 A | 11/1999 | Tybinkowski et al. |
| 6,188,743 B1 | 2/2001 | Tybinkowski et al. |
| 6,314,157 B1 * | 11/2001 | Tachizaki ............... A61B 6/035 378/197 |

(Continued)

FOREIGN PATENT DOCUMENTS

| | | |
|---|---|---|
| CN | 101069644 A | 11/2007 |
| JP | 5-168619 A | 7/1993 |

(Continued)

OTHER PUBLICATIONS

Machine Translation of WO 2010/119850 published in Oct. 2010.*

(Continued)

*Primary Examiner* — Hoon Song
(74) *Attorney, Agent, or Firm* — Oblon, McClelland, Maier & Neustadt, L.L.P.

(57) ABSTRACT

A gantry of X-ray CT system according to an embodiment includes: a main frame; a disk-shaped base plate rotatably supported by main frame, and having an opening formed at a central portion thereof, the opening allowing a subject to enter and exit therethrough, and multiple mounting holes formed at portions outside the opening in a radial direction; and multiple rotator units inserted into the mounting holes and fixed to the base plate.

18 Claims, 3 Drawing Sheets

(56) References Cited

U.S. PATENT DOCUMENTS

| | | | | |
|---|---|---|---|---|
| 2007/0041507 A1* | 2/2007 | Kendall | ............... | A61B 6/4429 |
| | | | | 378/197 |
| 2007/0274436 A1 | 11/2007 | Harada et al. | | |
| 2011/0316538 A1* | 12/2011 | Kim | .................... | A61B 6/4435 |
| | | | | 324/318 |

FOREIGN PATENT DOCUMENTS

| | | | |
|---|---|---|---|
| JP | 8-279389 A | 10/1996 | |
| JP | 2001-520434 A | 10/2001 | |
| JP | 2007-37873 A | 2/2007 | |
| JP | 2008-173466 A | 7/2008 | |
| JP | 2009-285146 A | 12/2009 | |
| JP | WO 2010/119850 A1 | 10/2010 | |
| JP | WO 2010119850 A1 * | 10/2010 | ............. A61B 6/035 |

OTHER PUBLICATIONS

International Search Report and Written Opinion issued Nov. 27, 2012 in PCT/JP2012/071439 with English Translation of Category of Cited Documents.
Combined Office Action and Search Report issued Jan. 26, 2015 in Chinese Patent Application No. 201280022153.5 (with English Translation of Category of Cited Documents).

\* cited by examiner

US 9,668,330 B2

GANTRY OF X-RAY CT SYSTEM

CROSS-REFERENCE TO THE RELATED APPLICATION

This application is based on and claims the benefit of priority from International Application No. PCT/JP2012/071439, filed on Aug. 24, 2012 and Japanese Patent Application No. 2011-184828, filed on Aug. 26, 2011; the entire contents of which are incorporated herein by reference.

FIELD

Embodiments described herein relate generally to a gantry of X-ray CT system.

BACKGROUND

An X-ray CT system includes: a bed where to lay down a subject; a gantry configured to perform X-ray scanning on the subject lying down on the bed by irradiating the subject with X-rays; and an operation unit configured to be operated for movement of the bed, X-ray scanning, and so on.

The gantry has: a main frame; and a rotator rotatably supported by the main frame with a bearing. The rotator has: a cylindrical part; a side plate part provided at one end side of the cylindrical part; and rotator units, such as an X-ray tube, an X-ray detector, and a generator, arranged on an inner circumferential side of the cylindrical part. The side plate part has an opening formed at a central portion thereof, the opening allowing the subject lying down on the bed to enter and exit therethrough.

When the rotator is rotated, a high centrifugal force acts on heavy rotator units such as the X-ray tube and the generator. For this reason, the rotator units are arranged on the inner circumferential side of the cylindrical part, so that the cylindrical part receives the centrifugal force acting on the rotator units, and thereby prevents the rotator units from flying off due to the centrifugal force during the rotation of the rotator.

However, such a gantry for CT system as described above does not take the following points into consideration.

First, since the rotator is provided with the cylindrical part formed over the entire outer circumference of the rotator, the rotator is heavy. Additionally, since the production cost of the rotator increases substantially proportional to the weight of the rotator, such a heavy rotator requires high production cost.

Moreover, for the heavy rotator, the bearing configured to rotatably support the rotator and a DD motor (direct drive motor) configured to rotate the rotator need to be large in size. Accordingly, the cost of the gantry is increased.

Further, the rotator is made of a casted metal in many cases. Such a rotator made of a casted metal is in a shape having a cylindrical part and a side plate part. Accordingly, the rotator has to be processed in various directions in finishing processing. This increases the cost of finishing processing.

DETAILED DESCRIPTION

According to one embodiment, a gantry of X-ray CT system includes: a main frame; a disk-shaped base plate rotatably supported by the main frame, and having an opening formed at a central portion thereof, the opening allowing a subject to enter and exit therethrough, and multiple mounting holes formed at portions outside the opening in a radial direction; and multiple rotator units inserted into the mounting holes of the base plate and fixed to the base plate.

Various Embodiments will be described hereinafter with reference to the accompanying drawings.

First Embodiment

Figure 1:
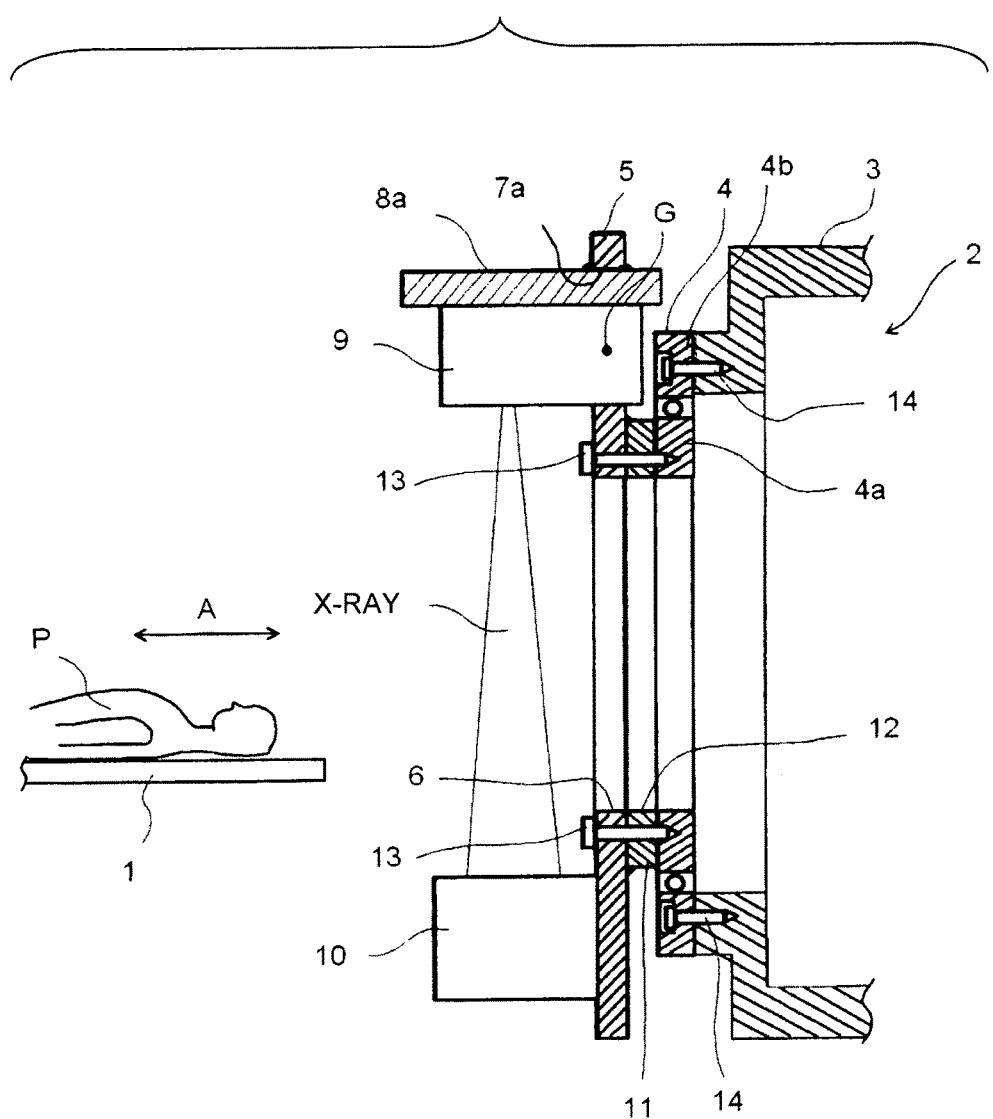
FIG. 1 is a side view of a vertical cross section of a rotator of a gantry of a first embodiment.

A first embodiment of the present invention will be described based on FIGS. 1 and 2. As shown in FIG. 1, an X-ray CT system includes: a bed 1 where to lay down a subject P; a gantry 2 configured to perform X-ray scanning on the subject P lying down on the bed 1 by irradiating the subject P with X-rays; and an operation unit (unillustrated) configured to be operated for movement of the bed 1, X-ray scanning with the gantry 2, and so on. The bed 1 is configured to be movable in directions in which the bed 1 enters and leaves the gantry 2 (the directions indicated by the arrow A).

The gantry 2 includes a main frame 3 and a base plate 5 rotatably supported by the main frame 3 with a bearing 4.

The base plate 5 is a disk-shaped member formed as an integral unit from an iron plate by, for example, punching. An opening 6 is formed at a central portion of the base plate 5, and allows the subject P lying down on the bed 1 to enter and exit therethrough. The subject P enters and exits through the opening 6, as the bed 1 on which the subject P lies down is moved in the directions indicated by the arrow A in which the bed 1 enters and leaves the gantry 2.

The base plate 5 have multiple mounting holes 7a, 7b, 7c, 7d, 7e, 7f, and 7g formed at portions thereof outside the opening 6 in a radial direction. Note that FIG. 1 shows only the single mounting hole 7a, and FIG. 2 shows the other mounting holes 7b to 7g.

A rectangularly-shaped iron mount plate 8a is inserted into and fixed to the mounting hole 7a. The mount plate 8a inserted into the mounting hole 7a passes through the mounting hole 7a, which is a through-hole, with its front and rear ends in an insertion direction both protruding from the mounting hole 7a. For fixation of the mount plate 8a inserted into the mounting hole 7a, the mount plate 8a inserted into the mounting hole 7a is welded or bolted to the base plate 5.

An X-ray tube 9 is fixed to the mount plate 8a. The X-ray tube 9 is a rotator unit configured to irradiate the subject P with X-rays. The fixation position of the X-ray tube 9 to the mount plate 8a is a position where the X-ray tube 9 is inserted into the mounting hole 7a, where the X-ray tube 9 has a center of gravity "G" located within a plane of rotation of the base plate 5, and where X-rays emitted from the X-ray tube 9 do not hit the base plate 5. The X-ray tube 9 is fixed to the mount plate 8a by screw-fastening or the like.

The mounting hole 7a has a shape that forms no gap between a peripheral edge portion of the mounting hole 7a and outer peripheral portions of the mount plate 8a and the X-ray tube 9 when the mount plate 8a and the X-ray tube 9 are inserted in the mounting hole 7a.

An X-ray detector 10 is fixed to a position at one side surface of the base plate 5, that is, the side surface opposite from the main frame 3, the position being opposite from the mount position of the X-ray tube 9 across the opening 6. The X-ray detector 10 is configured to detect X-rays transmitted through the subject P after the emission from the X-ray tube 9. The X-ray detector 10 is fixed to the side surface of the base plate 5 by screw-fastening or the like.

To the other side surface of the base plate 5, that is, the side surface on the main frame 3 side, a disk-shaped iron bearing-mounting plate 11 is fixed by welding or with a bolt. The bearing-mounting plate 11 has an opening 12 formed at a central portion thereof. The opening 12 has the same diameter as that of the opening 6 formed in the base plate 5, and allows the subject P lying down on the bed 1 to enter and exit therethrough. The bearing 4 is mounted between the bearing-mounting plate 11 and the main frame 3. The bearing 4 is mounted by fixing an inner ring 4a of the bearing 4 to the bearing-mounting plate 11 and the base plate 5 with multiple screws 13, and by fixing an outer ring 4b of the bearing 4 to the main frame 3 with multiple screws 14.

Figure 2:
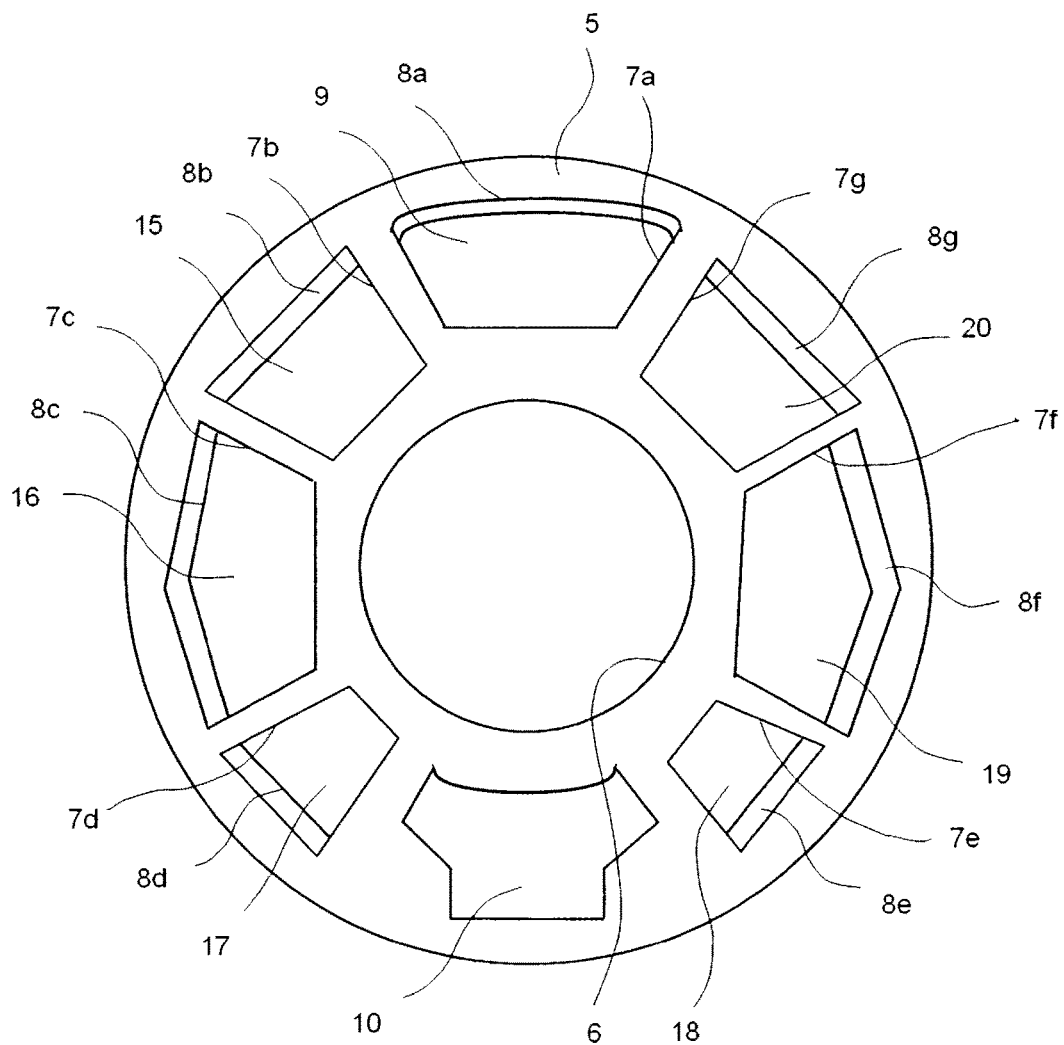
FIG. 2 is a front view of a base plate on which multiple mount plates and multiple rotator units are mounted.

As shown in FIG. 2, the multiple mounting holes 7b to 7g other than the mounting hole 7a illustrated in FIG. 1 are formed in the portions of the base plate 5 outside the opening 6 in the radial direction. The mounting holes 7a to 7g are arranged radially from the opening 6, which serves as the center.

Rectangularly-shaped iron mount plates 8b to 8g are individually inserted into and fixed to the respective mounting holes 7b to 7g. In the same manner as the mount plate 8a illustrated in FIG. 1, the mount plates 8b to 8g are individually inserted into the mounting holes 7b to 7g while passing through the mounting holes 7b to 7g with their both front and rear ends in the insertion direction protruding from the mounting holes 7b to 7g. For fixation of the mount plates 8b to 8g individually inserted into the mounting holes 7b to 7g, the mount plates 8b to 8g individually inserted into the mounting holes 7b to 7g are welded or bolted to the base plate 5.

For example, a generator 15, which is a rotator unit configured to generate high-voltage electricity to be supplied to the X-ray tube 9, is fixed to the mount plate 8b. A generator 16, which is a rotator unit configured to generate high-voltage electricity to be supplied to the X-ray tube 9, is fixed to the mount plate 8c. A rotator power supply 17, which is a rotator unit configured to generate electricity to be supplied to a rotation-side control board 18, is fixed to the mount plate 8d. The rotation-side control board 18, which is a rotator unit configured to control the rotation side, is fixed to the mount plate 8e. A balance weight 19, which is a rotator unit configured to balance the weight of the base plate 5, is fixed to the mount plate 8f. A cooler 20, which is a rotator unit configured to cool the X-ray tube 9, is fixed to the mount plate 8g (hereinafter, these units 9 and 15 to 20 are referred to as the rotator units 9 and 15 to 20, as appropriate).

The positions where the mounting holes 7a to 7g are formed are determined in consideration of the weights of the rotator units 9 and 15 to 20 individually fixed to the mounting holes 7a to 7g. When the rotator units 9 and 15 to are fixed, the center of gravity of the base plate 5 coincides with a center of rotation of the base plate 5.

The fixation positions of the individual rotator units 15 to 20 to the mount plates 8b to 8g are positions where the rotator units 15 to 20 are individually inserted into the mounting holes 7b to 7g and where the rotator units 15 to 20 each have a center of gravity located within the plane of rotation of the base plate 5. The individual rotator units 15 to 20 are fixed to the mount plates 8b to 8g by screw-fastening or the like.

The mounting holes 7b to 7g have such shapes that when the mount plates 8b to 8g and the rotator units 15 to 20 are individually inserted into the mounting holes 7b to 7g, no gap is formed between peripheral edge portions of the mounting holes 7b to 7g and outer peripheral portions of the mount plates 8b to 8g and the rotator units 15 to 20.

In the gantry 2 having the above-described configuration, the disk-shaped base plate 5 is rotatably supported by the main frame 3 with the bearing 4; the mount plates 8a to 8g are individually inserted into and fixed to the mounting holes 7a to 7g formed in the base plate 5; and the rotator units (the X-ray tube 9, the generators 15 and 16, the rotator power supply 17, the rotation-side control board 18, the balance weight 19, the cooler 20) are respectively fixed to the mount plates 8a to 8g. Further, the base plate 5 receives a centrifugal force acting on the rotator units 9 and 15 to 20 when the base plate 5 is rotated.

Hence, there is no need to provide the entire outer circumference of the base plate 5 with a cylindrical part described in the conventional example as a member to prevent the rotator units 9 and 15 to 20 from flying off from the base plate 5 during the rotation of the base plate 5. Thus, the weight of the base plate 5 can be reduced.

In addition, the weight reduction of the base plate 5 enables size reductions of the bearing 4 configured to rotatably support the base plate 5 and a DD motor configured to rotate the base plate 5. The weight reduction of the base plate 5 and the size reductions of the bearing 4 and the DD motor make it possible to reduce the cost of the gantry 2.

Moreover, since the base plate 5 and the mount plates 8a to 8g are members having a simple plate shape, the base plate 5 and the mount plates 8a to 8g are easy to manufacture. From this point also, a cost reduction of the gantry 2 is achieved.

Further, the bearing-mounting plate 11 is formed separately from the base plate 5, and the bearing-mounting plate 11 is welded or bolted to the base plate 5. Accordingly, the base plate 5 can be formed into a simple shape in comparison with a case where a member corresponding to the bearing-mounting plate 11 is formed integrally with the base plate 5. From this point also, a further cost reduction of the gantry 2 is achieved. The bearing-mounting plate 11 welded or bolted to the base plate 5 functions as a reinforcing member for the base plate 5. By welding or bolting the bearing-mounting plate 11 to the base plate 5, the strength of the base plate 5 can be improved.

The rotator units 9 and 15 to 20 are fixed to the base plate 5 by: welding or bolting the mount plates 8a to 8g individually inserted into the mounting holes 7a to 7g to the base plate 5 in the state that both of the front and rear ends of each mount plate in the insertion direction protrude from the mounting holes 7a to 7g; and then, for example, screw-fastening the rotator units 9 and 15 to 20 onto the mount plates 8a to 8g. Accordingly, it is possible to stabilize the fixed state of the rotator units 9 and 15 to 20 to the base plate 5.

Moreover, the rotator units 9 and 15 to 20 are fixed to the base plate 5 with the centers of gravity of the rotator units 9 and 15 to 20 located within the plane of rotation of the base plate 5. Accordingly, even when the rotation speed of the base plate 5 is increased, thereby increasing a centrifugal force acting on the rotator units 9 and 15 to 20, the base plate 5 can surely receive such a centrifugal force. This increases the performance to prevent the rotator units 9 and 15 to 20 from flying off due to a centrifugal force, thus improving the reliability of the gantry 2.

The X-ray tube 9, which is one of the rotator units, is fixed at such a position that emitted X-rays do not hit the base plate 5. Accordingly, the precision of X-ray scanning is improved.

The positions where the mounting holes 7a to 7g are formed in the base plate 5 are determined in consideration of the weights of the rotator units 9 and 15 to 20 individually fixed to the mounting holes 7a to 7g. When the rotator units 9 and 15 to 20 are fixed, the center of gravity of the base plate 5 coincides with the center of rotation of the base plate 5. Accordingly, when the base plate 5 is rotated for X-ray scanning, the base plate 5 is smoothly rotated.

Note that the X-ray detector 10 is a member configured to detect X-rays transmitted through the subject P after being emitted from the X-ray tube 9. Accordingly, the X-ray detector 10 is desirably fixed to the base plate 5 without being inserted into the mounting holes.

Since the base plate 5 can be manufactured easily by, for example, punching a plate, the thickness dimension of the base plate 5 can be altered as appropriate according to the rotation speed specification of the gantry 2. In addition, by using the base plate 5 having an optimal thickness dimension according to the rotation speed specification, the strength of the base plate 5 against a centrifugal force can be ensured, and the reliability of the gantry 2 can be increased.

Note that, in this embodiment, the description has been given by taking the example where the base plate 5 and the mount plates 8a to 8g are made of iron. However, the material of the base plate 5 and the mount plates 8a to 8g is not particularly limited. It is possible to use a different material, for example, an aluminum alloy or the like, capable of ensuring a desired strength.

Moreover, in this embodiment, the fixation of the rotator units 9 and 15 to 20 to the base plate 5 is described by taking the example where the rotator units 9 and 15 to 20 are fixed to the mount plates 8a to 8g by screw-fastening or the like, with the mount plates 8a to 8g individually inserted into and fixed to the mounting holes 7a to 7g while passing through the mounting holes 7a to 7g. Nevertheless, the rotator units 9 and 15 to 20 may be fixed to the base plate 5 without using the mount plates 8a to 8g. Specifically, the rotator units 9 and 15 to 20 may be directly inserted into the mounting holes 7a to 7g while passing through the mounting holes 7a to 7g individually, and then fixed by screw-fastening or the like.

Second Embodiment

Figure 3:
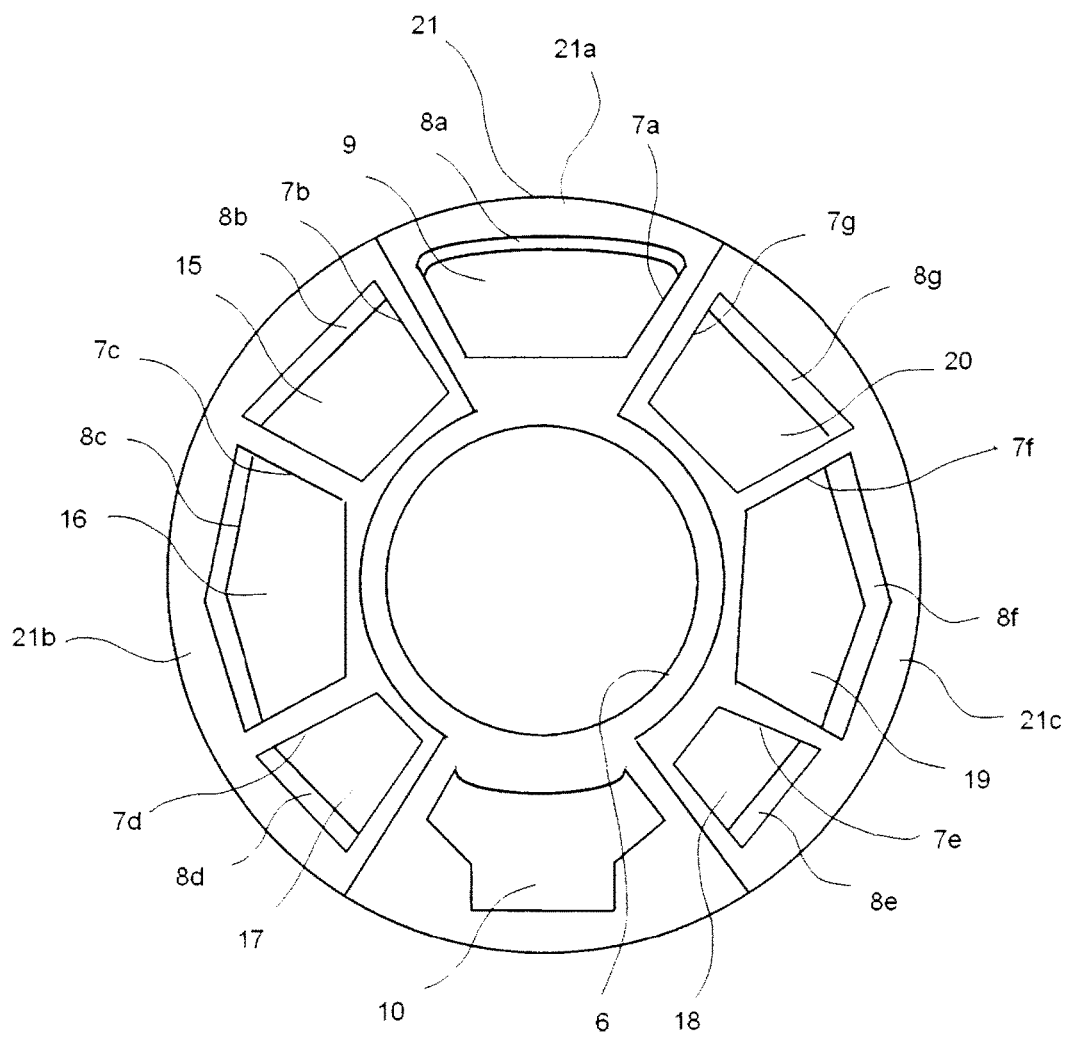
FIG. 3 is a front view of a base plate of a second embodiment on which the multiple mount plates and multiple rotator units are mounted.

A second embodiment of the present invention will be described based on FIG. 3. Note that the same reference signs denote the same constituents as those illustrated in FIGS. 1 and 2, and repetition of the description will be omitted.

The second embodiment differs from the first embodiment in that a base plate 21 is used in place of the base plate 5 described in the first embodiment. The other aspects are the same.

The base plate 21 of the second embodiment is formed by joining three divided base plates 21a, 21b, and 21c together into a disk shape. The divided base plates 21a and 21b, which are adjacent to each other, are joined together using a bolt; furthermore, the same holds true for the divided base plates 21a and 21c, which are adjacent to each other.

The divided base plate 21a has: the opening 6 formed at a central portion thereof; and the mounting hole 7a formed on one end side thereof. The mount plate 8a and the X-ray tube 9 are inserted into and fixed to the mounting hole 7a. The X-ray detector 10 is fixed by screw-fastening or the like to a position at a side surface of the divided base plate 21a, the position being opposite from the mounting hole 7a across the opening 6.

The divided base plate 21b has an outer appearance formed into a substantially circular sector shape. The three mounting holes 7b, 7c, and 7d are formed in the divided base plate 21b. The mount plate 8b and the generator 15 are inserted into and fixed to the mounting hole 7b. The mount plate 8c and the generator 16 are inserted into and fixed to the mounting hole 7c. The mount plate 8d and the rotator power supply 17 are inserted into and fixed to the mounting hole 7d.

The divided base plate 21c has an outer appearance formed into a substantially circular sector shape. The three mounting holes 7e, 7f, and 7g are formed in the divided base plate 21c. The mount plate 8e and the rotation-side control board 18 are inserted into and fixed to the mounting hole 7e. The mount plate 8f and the balance weight 19 are inserted into and fixed to the mounting hole 7f. The mount plate 8g and the cooler 20 are inserted into and fixed to the mounting hole 7g.

The divided base plate 21a is formed to have a thickness dimension larger than those of the divided base plates 21b and 21c.

The base plate 21 having the above-described configuration is formed of the three divided base plates 21a, 21b, and 21c joined together. Hence, the manufacturing, transportation, storage, and so forth can be done easily in comparison with a case where the base plate 21 is manufactured as an integral unit.

Moreover, by being divided, the divided base plates 21a, 21b, and 21c can be adjusted as appropriate in terms of the thickness dimension. For example, as to the divided base plate 21a to which the X-ray tube 9 and the X-ray detector 10 are fixed with a certain positional relation maintained therebetween by preventing a deformation during a rotation, the strength is increased by increasing the thickness dimension, thus improving the reliability. Meanwhile, as to the divided base plates 21b and 21c which do not bring about a problem even if deformed to some extent, a cost reduction is achieved by decreasing the thickness dimensions.

The gantry 2 of the embodiment described above includes: the main frame 3; the disk-shaped base plate 5 rotatably supported by the main frame 3 with the bearing 4, and having the opening 6 formed at the central portion, the opening allowing the subject P to enter and exit therethrough, and the multiple mounting holes 7a to 7g formed at portions outside the opening 6 in the radial direction; and the multiple rotator units 9 and 15 to 20 inserted into the mounting holes 7a to 7g and fixed to the base plate 5. Hence, the weight of the base plate 5 can be reduced. The weight reduction of the base plate 5 enables size reductions of the bearing 4 and the DD motor configured to rotate the base plate 5. The weight reduction of the base plate 5 and the size reductions of the bearing 4 and the DD motor make it possible to reduce the cost of the gantry 2.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A gantry of X-ray CT system, comprising:
a main frame;
a disk-shaped base plate rotatably supported by the main frame, and having
an opening formed at a central portion thereof, the opening allowing a subject to enter and exit therethrough, and
a plurality of mounting holes formed at portions thereof outside the opening in a radial direction; and
a plurality of rotator units inserted into the mounting holes of the base plate and fixed to the base plate,
wherein the plurality of mounting holes are formed at such positions that a center of gravity of the base plate with the rotator units fixed to the mounting holes coincides with a center of rotation of the base plate.

2. The gantry of X-ray CT system according to claim 1, comprising: mount plates inserted into and fixed to the mounting holes and configured to fix the rotator units to the mounting holes.

3. The gantry of X-ray CT system according to claim 1, wherein the rotator units each have a center of gravity located within a plane of rotation of the base plate.

4. The gantry of X-ray CT system according to claim 2, wherein the rotator units each have a center of gravity located within a plane of rotation of the base plate.

5. The gantry of X-ray CT system according to claim 1, wherein
one of the rotator units is an X-ray tube configured to emit X-rays, and
the X-ray tube is fixed at such a position that the emitted X-rays do not hit the base plate.

6. The gantry of X-ray CT system according to claim 2, wherein
one of the rotator units is an X-ray tube configured to emit X-rays, and
the X-ray tube is fixed at such a position that the emitted X-rays do not hit the base plate.

7. The gantry of X-ray CT system according to claim 1, wherein the base plate is formed as an integral unit.

8. The gantry of X-ray CT system according to claim 2, wherein the base plate is formed as an integral unit.

9. The gantry of X-ray CT system according to claim 1, wherein the base plate is formed of a plurality of divided base plates joined together.

10. The gantry of X-ray CT system according to claim 2, wherein the base plate is formed of a plurality of divided base plates joined together.

11. The gantry of X-ray CT system according to claim 9, wherein the plurality of divided base plates have different thickness dimensions from each other depending on the rotator units fixed to the divided base plates.

12. The gantry of X-ray CT system according to claim 10, wherein the plurality of divided base plates have different thickness dimensions from each other depending on the rotator units fixed to the divided base plates.

13. A gantry of X-ray CT system comprising:
a main frame;
a disk-shaped base plate rotatably supported by the main frame, and having
a circular opening formed at a central portion thereof, the opening allowing a subject to enter and exit therethrough, and
a plurality of mounting holes formed at portions thereof outside the opening in a radial direction;
a plurality of rotator units inserted into the mounting holes of the base plate and fixed to the base plate; and
an X-ray detector configured to detect X-rays, wherein
the base plate is formed of a plurality of divided base plates arranged adjacent each other in a plane of rotation of the base plate and joined together,
one of the rotator units is an X-ray tube configured to emit X-rays,
the X-ray detector is arranged at a position opposite from the X-ray tube across the opening,
the X-ray tube and the X-ray detector are fixed to the same divided base plate, and
the divided base plate to which the X-ray tube and the X-ray detector are fixed is formed to have the circular opening being a through-hole.

14. The gantry of X-ray CT system according to claim 13, wherein
the divided base plate to which the X-ray tube and the X-ray detector are fixed is formed into a shape having sector plates and a circular frame provided between the sector plates.

15. The gantry of X-ray CT system according to claim 13, wherein the divided base plate to which the X-ray tube and the X-ray detector are fixed is formed to have a larger thickness dimension than the other divided base plates.

16. The gantry of X-ray CT system according to claim 14, wherein the divided base plate to which the X-ray tube and the X-ray detector are fixed is formed to have a larger thickness dimension than the other divided base plates.

17. The gantry of X-ray CT system according to claim 1, wherein the mounting holes are through-holes.

18. A gantry of X-ray CT system, comprising:
a main frame;
a disk-shaped base plate rotatably supported by the main frame, and having
an opening formed at a central portion thereof, the opening allowing a subject to enter and exit therethrough, and
a plurality of mounting holes formed at portions thereof outside the opening in a radial direction;
a plurality of rotator units inserted into the mounting holes of the base plate and fixed to the base plate; and
an X-ray detector configured to detect X-rays, wherein
one of the rotator units is an X-ray tube configured to emit X-rays,
the X-ray detector is arranged at a position opposite from the X-ray tube across the opening,
a center of gravity of the X-ray tube is located within a plane of rotation of the base plate, and
a center of the X-ray tube in a direction normal to the plane of rotation of the base plate is located on an opposite side to the main frame with respect to the plane of rotation of the base plate.

* * * * *